United States Patent
Okubo et al.

(10) Patent No.: US 9,175,133 B2
(45) Date of Patent: Nov. 3, 2015

(54) POLYESTER WITH EXCELLENT THERMOSTABILITY AND MANUFACTURING METHOD THEREFOR

(75) Inventors: Takuro Okubo, Nagoya (JP); Youichiro Tanaka, Nagoya (JP); Kunihiro Morimoto, Otsu (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/114,937

(22) PCT Filed: Aug. 24, 2012

(86) PCT No.: PCT/JP2012/071495
§ 371 (c)(1),
(2), (4) Date: Oct. 31, 2013

(87) PCT Pub. No.: WO2013/035559
PCT Pub. Date: Mar. 14, 2013

(65) Prior Publication Data
US 2014/0058059 A1     Feb. 27, 2014

(30) Foreign Application Priority Data

Sep. 6, 2011 (JP) .................................. 2011-193783

(51) Int. Cl.
| | | |
|---|---|---|
| C08G 63/183 | (2006.01) | |
| C08G 63/00 | (2006.01) | |
| C08G 63/672 | (2006.01) | |
| C08G 63/688 | (2006.01) | |
| C07C 29/76 | (2006.01) | |
| C07C 29/80 | (2006.01) | |

(52) U.S. Cl.
CPC .............. *C08G 63/183* (2013.01); *C07C 29/76* (2013.01); *C07C 29/80* (2013.01); *C08G 63/00* (2013.01); *C08G 63/672* (2013.01); *C08G 63/6886* (2013.01)

(58) Field of Classification Search
CPC .............. D01F 8/14; D01F 6/84; D04H 1/42; D04H 3/10; D04H 13/002; D04H 1/4391; D04H 1/565; D04H 3/16; D04H 1/465; C08G 63/672; C08G 63/6886; C08G 63/00; C08G 63/183; C08L 67/02; C08L 2666/02
USPC ........................ 528/272, 308, 295, 301, 308.1
See application file for complete search history.

(56) References Cited

U.S. PATENT DOCUMENTS 4,621,020 A * 11/1986 Tashiro et al. ................ 428/361

FOREIGN PATENT DOCUMENTS

| CN | 101046007 A | | 10/2007 |
|---|---|---|---|
| EP | 0272417 | * | 6/1988 |
| JP | 02-191626 | * | 7/1990 |
| JP | 02-191626 A | | 7/1990 |
| JP | 09-031170 A | | 2/1997 |
| JP | 2007-502325 A | | 2/2007 |
| JP | 2009-013094 A | | 1/2009 |
| JP | 2009-120568 A | | 6/2009 |
| JP | 2009-209145 A | | 9/2009 |
| WO | 2009/064515 A1 | | 5/2009 |
| WO | 2009/079213 A2 | | 6/2009 |

OTHER PUBLICATIONS

W.F. Tuley et al., "p-Toluic Acid," *Organic Syntheses*, Coll. vol. 3, p. 822 (1955); vol. 27, p. 86 (1947).
Klaus Anders et al., "Zum Mechanismus der p-Xylenbildung aus 2,4,4-Trimethyl-pentenen," Chem. Techn., 38. Jg., Heft 3, März 1986, pp. 116-119 (Abstract only).
The Chemical Society of Japan, 1986, No. 2, pp. 217-219 (partial translation).

* cited by examiner

*Primary Examiner* — Ling Choi
*Assistant Examiner* — Gennadiy Mesh
(74) *Attorney, Agent, or Firm* — DLA Piper LLP (US)

(57) ABSTRACT

A polyester has excellent thermostability with only a small reduction in intrinsic viscosity during melt molding. The polyester is obtained from a dicarboxylic acid, and/or an ester-forming derivative thereof, and an ethylene glycol, a catalyst selected from the group consisting of a titanium compound, aluminum compound and antimony compound, a phosphorous compound selected from the group consisting of phosphoric acid, trimethyl phosphate, ethyl diethylphosphonoacetate, 3,9-bis(2,6-di-t-butyl-4-methylphenoxy) -2,4,8, 10-tetraoxa-3,9-diphosphaspiro[5,5]undecane and tetrakis (2,4-di-t-butyl-5-methylphenyl) [1,1-biphenyl]-4,4'-diylbis-phosphonite, wherein the polyester contains 15 to 203 ppm of a sum of copolymerized 1,2-propanediol and/or uncopolymerized 1,2-propanediol wherein ethylene glycol is obtained from biomass and has content of 1,2-propanediol of 45 to 1000 ppm.

6 Claims, No Drawings

POLYESTER WITH EXCELLENT THERMOSTABILITY AND MANUFACTURING METHOD THEREFOR

TECHNICAL FIELD

This disclosure relates to polyester with excellent thermostability. More specifically, the disclosure relates to polyester with only a small reduction in intrinsic viscosity during melt molding and a manufacturing method therefor.

BACKGROUND

Since polyester has excellent mechanical strength, chemical stability and transparency, as well as being inexpensive, it is one of the most commonly used synthetic resins throughout the world in various applications, including fibers, films, sheets and containers. Of all kinds of polyester, polyethylene terephthalate is particularly advantageously used because of its excellence in general versatility and practical applicability.

Generally speaking, polyethylene terephthalate is manufactured from terephthalic acid, or an ester-forming derivative thereof, and ethylene glycol, and such raw materials are normally obtained from fossil resources. Although oil, a fossil resource, is an important raw material in the chemical industry, it is a cause of global warming and other environmental problems as it generates large quantities of carbon dioxide during manufacturing and incineration disposal, not to mention concerns over future depletion. Such being the case, much attention has been focused on the use of reclaimed materials and materials with a low environmental load.

Biomass resources are produced by plants from water and carbon dioxide through photosynthesis, and take the forms of starch, carbohydrate, cellulose, lignin, and the like. Since biomass resources take in carbon dioxide as one of their input materials during their formation processes, any material that uses a biomass resource does not produce any net carbon dioxide emissions in its life cycle, even if decomposed into carbon dioxide and water during post-use incineration disposal. As this carbon dioxide may, under certain circumstances, be recycled by plants, biomass resources can be regarded as renewable resources. Using such biomass resources as an alternative to oil resources helps preserve fossil resources and reduce carbon dioxide emissions.

Against this background, ways to synthesize polyester, a very high-demand polymer, from renewable biomass resources are being studied. Examples include a report on polyethylene terephthalate (PET) synthesized from biomass-derived ethylene glycol (Chinese Patent Publication No. 101046007). However, since biomass-derived ethylene glycol is low in purity, any polymer obtained from it exhibits a problem of thermostability in the form of a low melting point.

As a method to overcome this problem, an adsorption treatment designed to remove impurities from biomass-derived ethylene glycol using activated carbon has been disclosed (Japanese Unexamined Patent Publication (Kokai) No. 2009-209145). That method has made it possible to obtain polymers with melting points comparable to those synthesized from fossil resource-based glycols.

After chipping, polyester is usually melted again and molded, and is subjected to a thermal history approaching 300° C. in the process. Compared to fossil resource-based polymers, polymers synthesized from biomass-derived glycol have poor thermostability. In this regard, we observed a problem in that the above process promotes decomposition reaction in such polymers and causes yellowing and a reduction in viscosity, i.e., a reduction in molecular weight, leading to several undesirable phenomena, including an increased soiling of the die of the molding machine and generation of foreign matter.

It could therefore be helpful to provide a polyester that has excellent thermostability during melt molding, namely, to provide a polyester with only a small reduction in intrinsic viscosity during melt molding, as well as a manufacturing method therefor.

SUMMARY

We provide a polyester obtained from a dicarboxylic acid and/or an ester-forming derivative thereof, and a diol, containing 15 to 500 ppm of a 1,2-propanediol-derived component.

We also provide a method of manufacturing polyester including subjecting a dicarboxylic acid and/or an ester-forming derivative thereof, and a diol to an esterification or ester interchange reaction and performing a condensation polymerization reaction under reduced pressure, wherein the diol has a 1,2-propanediol content of 45 to 1,000 ppm.

DETAILED DESCRIPTION

Our polyesters are obtained from a dicarboxylic acid and/or an ester-forming derivative thereof, and a diol and contain 15 to 500 ppm of a 1,2-propanediol-derived component.

Since the polyester is designed to contain 15 to 500 ppm of a 1,2-propanediol-derived component, it has excellent thermostability during melt molding, namely only a small reduction in intrinsic viscosity during melt molding. With the polyester, soiling of molding machine dies and generation of foreign matter is limited. This makes continuous operation possible, thus increasing production efficiency.

We discovered that thermostability during melt molding improved as the purity increased. However, we serendipitously made a further discovery that 1,2 propanediol, an impurity present in biomass-derived glycol, provided the polyester with better thermostability during melt molding than a polyester obtained from a fossil resource-based glycol, i.e., successfully limiting the reduction in its intrinsic viscosity during melt molding, when kept in a certain concentration range rather than removed as a mere impurity. More specifically, we discovered a polyester containing 15 to 500 ppm of a 1,2-propanediol-derived component excelled in thermostability during melt molding, namely exhibiting only a small reduction in intrinsic viscosity during melt molding.

Although the mechanism of this improvement in thermostability is not yet fully understood, it may be explained as follows: Generally speaking, diols have the capacity to cyclize and become a bidentate ligand in relation to a metal such as a condensation polymerization catalyst. 1,2-Propanediol may be considered to be a compound in which a methyl group has bonded to one of the two carbon atoms present in ethylene glycol as a side chain. Generally speaking, the greater the number of substituent groups of a chain molecule is and the bulkier such substituent groups are, the more likely the chain molecule cyclizes due to a stereoscopic overhang effect. For this reason, despite both being diols, 1,2-propanediol is more likely to cyclize and become a bidentate ligand in relation to a metal than ethylene glycol as it is considered to have a methyl group as a side chain. Along these lines, a minute amount of 1,2-propanediol contained in a polyester is thought to have become a bidentate ligand in relation to the metal, a polymerization catalyst, on a preferential basis. This, in turn, is believed to improve thermostability during melt molding by limiting the thermal decomposition reaction involving a metal catalyst without suppressing its polymerization activity.

It is preferable that the polyester contains, as copolymerization components, at least one selected from a 5-sulfoisophthalic acid salt, and/or an ester-forming derivative thereof, and a polyoxyalkylene glycol with a molecular weight of 500 to 20,000, as it amplifies the effect of improving the thermostability of the polyester. It is preferable that the diol takes part in the synthesis of polyester be ethylene glycol.

Moldings produced from such a highly thermostable polyester exhibit high stability in product quality and excellent mechanical characteristics, not to mention excellent processability during molding.

The manufacturing method for the polyester uses a diol whose 1,2-propanediol content is 45 to 1000 ppm as part of a method to manufacture polyester by having a dicarboxylic acid, and/or an ester-forming derivative thereof, and a diol undergo an esterification or ester interchange reaction, followed by a condensation polymerization reaction under reduced pressure. It is preferable that such a diol be ethylene glycol.

It is preferable that the diol used for the manufacture of the polyester contain 45 to 1000 ppm of 1,2-propanediol as it makes it possible to prepare a polyester with excellent thermostability. As such a diol, ethylene glycol is preferable.

It is preferable that the manufacturing method for such a diol combine distillation, performed with 40 or more theoretical plates at a reflux ratio of 10 or more, and adsorption separation, performed with an activated carbon filter layer at a space velocity of 0.1 to 1.1 $hr^{-1}$, to purify the raw diol. It is preferable that the raw diol be biomass-derived ethylene glycol.

The polyester is obtained from a dicarboxylic acid, and/or an ester-forming derivative thereof, and a diol and contains 15 to 500 ppm of a 1,2-propanediol-derived component. If the polyester contains more of a 1,2-propanediol-derived component than this range, the thermostability of the polyester deteriorates, while, if it contains less of a 1,2-propanediol-derived component than the same range, the polyester cannot benefit from a thermostability improvement effect.

A 1,2-Propanediol-derived component represents an aggregate of the 1,2-propanediol detected when polyester is decomposed, and is a total amount of 1,2-propanediol based on the 1,2-propanediol-derived structure copolymerized into the polymer chain, and 1,2-propanediol mixed in the midst of the polymer. Namely, such 1,2-propanediol may be partially copolymerized into the backbone chain of the polyester or contained as 1,2-propanediol monomers without being copolymerized.

Examples of a dicarboxylic acid and/or an ester-forming derivative thereof as monomer raw materials for the polyester include terephthalic acid, isophthalic acid, 2,6-naphthalene dicarboxylic acid, diphenyl-4, 4-dicarboxylic acid, and any ester-forming derivative thereof. Ester-forming derivatives include, among other things, lower alkyl esters, anhydrides and acyl chlorides of such dicarboxylic acids, and, of them, methyl esters, ethyl esters, hydroxyethyl esters and the like are preferably used. More preferable forms of a dicarboxylic acid and/or an ester-forming derivative thereof are terephthalic acid and/or a dimethyl ester thereof.

Terephthalic acid and/or a dimethyl ester thereof may be biomass-derived. As there are no specific restrictions on the method to obtain biomass-derived terephthalic acid, any method may be used. Examples include a processing sequence comprising the extraction of isobutanol from corn, sugar or wood, its conversion into isobutylene, its dimerization to obtain isooctane, synthesis of p-xylene using a documented method involving radical cleavage, recombination and cyclization (Chemische, Technik, vol. 38, N0.3, p.p. 116-119; 1986), and its oxidation to obtain terephthalic acid (WO2009-079213).

Other methods include the synthesis of p-cymene from cineole obtained from plants of the genus *Eucalyptus* (Bulletin of Chemical Society of Japan, (2), p.p. 217-219; 1986), followed by the production of terephthalic acid via p-methyl benzoic acid (Organic Syntheses, 27; 1947). There is yet another method in which terephthalic acid is obtained from furan dicarboxylic acid and ethylene via a Diels-Alder reaction (WO2009-064515). The biomass-derived terephthalic acid obtained in this manner may be further converted into an ester-forming derivative.

It is preferable that the diol contain 45 to 1000 ppm of 1,2-propanediol. Examples of such a diol include ethylene glycol, 1,3-propanediol, 1,4-butanediol, and cyclohexanedimethanol, and, of them, ethylene glycol is preferable. Since biomass-derived ethylene glycol often contains 1,2-propanediol, it is more preferable that biomass-derived ethylene glycol be used after adjusting its 1,2-propanediol content through purification.

As there are no specific restrictions on the method to obtain biomass-derived ethylene glycol, any method may be used. For instance, there is a method that uses corn, sugarcane, wheat, stems of crops, or some other biomass resource. Such biomass resources are first converted into starch, which, in turn, is converted into glucose using water and an enzyme, and glucose is then converted into sorbitol via a hydrogenation reaction, with sorbitol continuing to undergo a hydrogenation reaction at a constant temperature and pressure in the presence of a catalyst to become a mixture of various glycols, followed by purification to obtain ethylene glycol.

Other methods include a processing sequence comprising an production of bioethanol from sugarcane and other carbohydrate-based crops using a biological processing method, conversion into ethylene, and production of ethylene glycol via ethylene oxide. There is yet another method in which glycerin is obtained from a biomass resource, followed by the production of ethylene glycol via ethylene oxide.

Though the ethylene glycol obtained in this manner contains various impurities, it is actually preferable to purify it such that it contains 1,2-propanediol, one of the impurities, by 45 to 1000 ppm. Purification methods for biomass-derived ethylene glycol include distillation purification, extraction separation, adsorption separation, and membrane separation, and the preferred method is to combine distillation purification and adsorption separation.

With distillation purification, it is preferable that the number of theoretical plates be 40 or more, though, from an economic viewpoint, the preferred number is 60 or less. It is preferable that the distillation reflux ratio be 10 or more, though, from an economic viewpoint, the preferred reflux ratio is 20 or less. There are no specific restrictions on the type of distillation tower, and examples include a packed tower and plate tower. Distillation may take place in a single distillation tower or two or more distillation towers. The type of distillation process may be either batch or continuous, but, for industrial production, a continuous process is preferable.

With adsorption separation, it is preferable that, before attempting to remove impurities by activated carbon adsorption, the biomass-derived ethylene glycol be heated to convert impurities into compounds that are amenable to activated carbon adsorption. It is preferable that the heating duration and temperature be 15 to 30 hours and 190 to 200° C., respectively. If the heating duration is too short or the heating temperature is too low, some of the impurities may not be converted into compounds that are amenable to activated carbon adsorption. After heating, the biomass-derived ethylene glycol is first cooled and then brought into contact with activated carbon. It is preferable that the temperature after cooling be 0 to 100° C. Examples of activated carbon include activated carbon from coal and activated carbon from wood. Preferable commercial activated carbon products include coal-based DIAHOPE 008 (manufactured by Calgon Carbon Japan K.K.) and wood-based Taiko SGA (manufactured by Futamura Chemical Industries Co., Ltd.). Of them, wood-based Taiko SGA is particularly preferable. In terms of shape, examples of activated carbon include powder activated carbon, granular activated carbon and fibrous activated carbon, and, of them, granular activated carbon is preferable. It is preferable that the particle size of granular activated carbon be 1 to 3 mm in terms of maximum diameter. It is preferable that the infiltration percolation method be used to bring activated carbon into contact with biomass-derived ethylene glycol. To secure an adequate contact duration, it is preferable that the thickness of the activated carbon filter layer be 200 to 500 cm, more preferably 200 to 300 cm. It is further preferable that biomass-derived ethylene glycol and activated carbon be brought into contact at a space velocity of 0.1 to 1.1 $hr^{-1}$. Space velocity means the quantity of the feed material (volume) that has been passed through the packed material per hour in terms of the multiple of the quantity of the packed material (volume) as interpreted as velocity. In this regard, distillation purification and adsorption separation may take place in either order.

When biomass-derived raw materials are used, the biobased content of the obtained polyester is determined by measuring the concentration of the radioactive carbon $^{14}C$ (pMC). The concentration of the radioactive carbon $^{14}C$ can be measured in accordance with a radiocarbon concentration measurement method as described below. Using an accelerator mass spectrometer (AMS), the radiocarbon concentration measurement method physically separates the atoms of carbon isotopes ($^{12}C$, $^{13}C$ and $^{14}C$) contained in the analysis specimen using the weight difference and measures the abundance of those isotope atoms. Most carbon atoms are $^{12}C$, but its stable $^{13}C$ is also present at an abundance of about 1.1%. The carbon $^{14}C$ is a radioactive isotope with a half-life of about 5370 years, and its abundance has been steadily decreasing due to radioactive decay. It takes another 226,000 years for it to all but totally decay. The Earth's upper atmosphere is constantly bombarded by cosmic rays, and minute quantities of $^{14}C$ are continuously produced. This $^{14}C$ replenishment balances out radioactive decay, and keeps the atmospheric concentration of $^{14}C$ roughly constant (approx. 1 part per trillion of all carbon atoms). Such $^{14}C$ immediately undergoes an isotopic exchange reaction with the carbon dioxide $^{12}C$, and carbon dioxide containing $^{14}C$ is generated in the process. Since plants grow by taking in atmospheric carbon dioxide and engaging in photosynthesis, they always contain $^{14}C$ at a certain concentration. In contrast, oil, coal and natural gas, as fossil resources, contain hardly any $^{14}C$ as their shares of $^{14}C$, which were initially present, have over the eons virtually completely decayed. This makes it possible to determine the content of biomass-derived carbon and that of fossil resource-based carbon by measuring the concentration of $^{14}C$. In this regard, it is common to use a standard that sets at 100% the concentration of $^{14}C$ in the natural carbon cycle in the 1950s, with oxalic acid designated as the standard substance (supplied by National Institute of Standards and Technology, NIST). Under this standard, a quantity called "pMC (percent Modern Carbon)" is calculated using the following formula:

$$pMC = (^{14}Csa / ^{14}C50) \times 100$$

where $^{14}C50$ is the $^{14}C$ concentration of the standard substance (representing the concentration of $^{14}C$ in the natural carbon cycle in the 1950s). $^{14}Csa$ is the $^{14}C$ concentration of the measurement specimen.

The atmospheric concentration of $^{14}C$ as of 2011 based on the above measurement method is known to be 105 pMC (percent Modern Carbon), so that any 100% biomass-derived material is expected to more or less register the same pMC value of 105. In contrast, the $^{14}C$ concentration of fossil resources is always 0 pMC. Based on this fact, the biobased content of a given material can be calculated by allocating a biobased content of 100% to 105 pMC and a biobased content of 0% to 0 pMC. Namely, the measured $^{14}C$ concentration value X (pMC) is converted into the corresponding biobased content value Y (%) using the following formula:

$$105:100 = X:Y$$

It is preferable that the biobased content of the obtained polyester be 10% or more, more preferably 15% or more.

It is preferable that the polyester be polyethylene terephthalate obtained from terephthalic acid and/or a dimethyl ester thereof as the component comprising a dicarboxylic acid and/or an ester-forming derivative (hereinafter may be abbreviated as the "dicarboxylic acid component"), on the one hand, and ethylene glycol as the diol component, on the other. Furthermore, a polyester copolymer mainly comprising ethylene terephthalate units exhibits a marked improvement in thermostability.

Examples of a copolymerization component of the polyester include dicarboxylic acid components, encompassing an aromatic dicarboxylic acid or any ester-forming derivative thereof such as isophthalic acid, a 5-sulfoisophthalic acid salt (e.g., lithium 5-sulfoisophthalate, potassium 5-sulfoisophthalate or sodium 5-sulfoisophthalate), phthalic acid or naphthalene-2,6-dicarboxylic acid, and an aliphatic dicarboxylic acid or any ester-forming derivative thereof such as succinic acid, adipic acid, pimelic acid, suberic acid, azelaic acid, sebacic acid, 1,9-nonane dicarboxylic acid or 1,12-dodecane dicarboxylic acid.

Examples of a copolymerization component of a polyester containing ethylene glycol as its main diol component include diols, encompassing 1,3-propanediol, 1,4-butanediol, 1, 5-pentanediol, 1, 6-hexanediol, a polyoxyalkylene glycol with a molecular weight of 500 to 20,000 (e.g., polyethylene glycol), diethylene glycol, 2-methyl-1,3-propanediol, and bisphenol A-ethylene oxide adduct.

Of them, 5-sulfoisophthalic acid salts such as lithium 5-sulfoisophthalate, potassium 5-sulfoisophthalate and sodium 5-sulfoisophthalate, ester-forming derivatives thereof, and polyoxyalkylene glycols with a molecular weight of 500 to 20,000 are preferable. The preferred form of a polyoxyalkylene glycol is polyethylene glycol, and polyethylene glycol with a molecular weight of 500 to 10,000 is particularly preferable.

It is preferable that, as copolymerization components, 5-sulfoisophthalic acid salts be contained by 0.1 to 10 mol % relative to the total dicarboxylic acid component as the main ingredient of the polyester. It is also preferable that, as a copolymerization component, a polyoxyalkylene glycol with a molecular weight of 500 to 20,000 be contained by 0.1 to 10.0 wt % relative to the weight of the obtained polyester.

Such copolymerization components may be used singly but they have a more pronounced thermostability improvement effect on the polyester if two or more are combined.

The polyester is commonly manufactured through either of the processes described below.

In process (A), low polymers are first obtained from terephthalic acid and an alkylene glycol through a direct esterification reaction, and a high-molecular weight polymer is then obtained through their condensation polymerization reaction. In process (B), low polymers are obtained from dimethyl terephthalate and an alkylene glycol through an ester interchange reaction, and a high-molecular weight polymer is then obtained through their condensation polymerization reaction.

In process (A) above, it is preferable that the reaction temperature and pressure be set at 250° C. or less and 1.2×100,000 Pa or more, respectively, during the direct esterified reaction. In the ensuing condensation polymerization reaction, it is preferable that the reaction temperature and pressure be set at 280° C. or less and 110 Pa or more, respectively, though, the lower the pressure, the shorter the polymerization time becomes. If a higher temperature and lower pressure than the above are used in either of the reaction steps, 1,2-propanediol, which has a lower boiling point than ethylene glycol, may preferentially evaporate, leading to a failure for the polyester to contain the necessary amount of 1,2-propanediol.

In process (B) above, it is preferable that the reaction temperature and pressure be set at 230° C. or less at atmospheric pressure or more, respectively, during the ester interchange reaction. In the ensuing condensation polymerization reaction, it is preferable that the reaction temperature and pressure be set at 280° C. or less and 110 Pa or more, respectively, though, the lower the pressure, the shorter the polymerization time becomes. As in process (A), if a higher temperature and lower pressure than the above are used in either of the reaction steps, 1,2-propanediol, which has a lower boiling point than ethylene glycol, may preferentially evaporate, leading to a failure for the polyester to contain the necessary amount of 1,2-propanediol.

Though the esterification reaction in process (A) progresses without a catalyst, a compound containing magnesium, manganese, calcium, cobalt, lithium, titanium or the like may be used as a catalyst in a similar manner as an ester interchange catalyst in process (B). Examples of a compound that may be used as a catalyst during the condensation polymerization reaction include a titanium compound, aluminum compound, tin compound, antimony compound, and germanium compound.

Specific examples of a magnesium compound suitable for use include magnesium oxide, magnesium hydroxide, magnesium alkoxide, magnesium acetate, and magnesium carbonate.

Specific examples of a manganese compound include manganese chloride, manganese bromide, manganese nitrate, manganese carbonate, manganese acetylacetonate, and manganese acetate.

Specific examples of a calcium compound include calcium oxide, calcium hydroxide, calcium alkoxide, calcium acetate, and calcium carbonate.

Specific examples of a cobalt compound include cobalt chloride, cobalt nitrate, cobalt carbonate, cobalt acetylacetonate, cobalt naphthenate, and cobalt acetate tetrahydrate.

Specific examples of a lithium compound include lithium oxide, lithium hydroxide, lithium alkoxide, lithium acetate, and lithium carbonate.

Examples of a titanium compound include a titanium complex, a titanium alkoxide such as tetra-i-propyl titanate, tetra-n-butyl titanate or tetra-n-butyl titanate tetramer, titanium oxide obtained from a hydrolysis of a titanium alkoxide, and titanium acetylacetonate. Of them, a titanium complex containing a multivalent carboxylic acid, and/or hydroxycarboxylic acid, and/or a polyhydric alcohol as chelating agents is preferable from the viewpoint of the thermostability and color tone of the polymer and cleanliness of the die area. Chelating agents for a titanium compound include lactic acid, citric acid, mannitol, and tripentaerythritol.

Aluminum compounds encompass, among other things, aluminum carboxylate, aluminum alkoxide, aluminum chelate compound and basic aluminum compound, and specific examples include aluminum acetate, aluminum hydroxide, aluminum carbonate, aluminum ethoxide, aluminum isopropoxide, aluminum acetylacetonate, and basic aluminum acetate.

Examples of a tin compound include monobutyl tin oxide, tin acetate, tin octylate, and tin alkoxide.

Examples of an antimony compound include antimony alkoxide, antimony glycolate, and antimony trioxide.

Examples of a germanium compound include germanium alkoxide, and germanium oxide.

Such metal compounds may be hydrates.

It is preferable that a phosphorus compound be added to the polyester as a stabilizer. Specific examples of such a phosphorus compound include phosphoric acid, trimethyl phosphate, and ethyl diethylphosphonoacetate. More preferable in terms of color tone and improved thermostability are trivalent phosphorus compounds such as 3,9-bis(2,6-di-t-butyl-4-methylphenoxy)-2,4,8,10-tetraoxa-3,9-diphosphaspiro[5,5]undecane (PEP-36, manufactured by ADEKA CORPORATION), as expressed with Formula (1) below, and tetrakis(2,4-di-t-butyl-5-methylphenyl) [1,1-b]phenyl]-4,4'-diylbisphosphonite (GSY-P101, manufactured by Osaki Industry Co., Ltd.), as expressed with Formula (2) below:

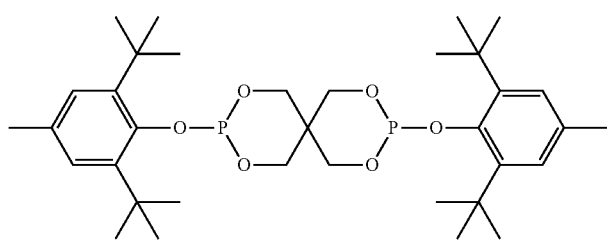

(1)

-continued

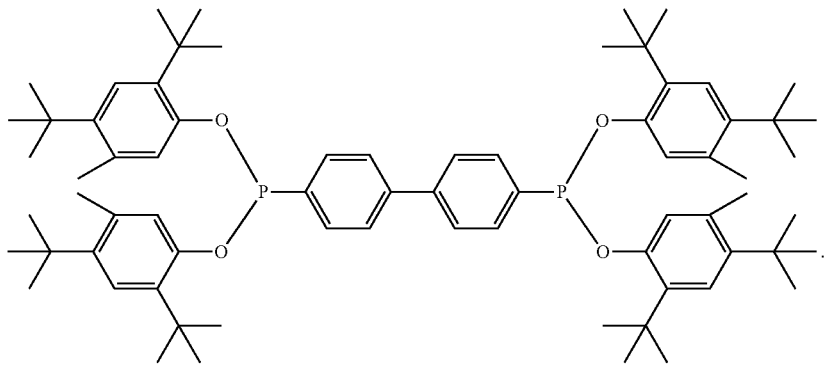

(2)

If needed, dyes used as color tone adjusting agents for resins and the like may also be added. Specific examples in terms of a color index generic name include Solvent Blue 104 and Solvent Blue 45, as blue-based color tone adjusting agents, and Solvent Violet 36, as a purple-based color tone adjusting agent—which are preferable as they exhibit relatively good thermostability at high temperatures and an excellent chromogenic property, while being free of halogens as common contributing factors to equipment corrosion. These may be used singly or in combination of two or more.

Other additives such as antioxidant, ultraviolet absorber, flame retardant, fluorescent brightening agent, matting agent, plasticizer and antifoam agent, may also be added as necessary.

To obtain a polyalkylene terephthalate with an even higher molecular weight, the polyalkylene terephthalate obtained through the method described above may be subjected to solid-state polymerization. Solid-state polymerization is performed through heat treatment in an inert gas atmosphere or under reduced pressure, though there are no specific restrictions on the equipment or method. The inert gas may be any gas as long as it is inert with polyester, and examples include nitrogen, helium, and carbon dioxide, with nitrogen preferred for economic efficiency. Regarding reduced pressure, the lower the pressure, the shorter the time required for a solid-state condensation polymerization reaction. Despite this advantage, however, it is preferable that the pressure be kept at 110 Pa or more from the viewpoint of retaining a 1,2-propanediol-derived component in the polyester.

Polyester products may also be recycled. More specifically, any discarded polyester is first subjected to a depolymerization reaction via the glycol component to obtain bis (hydroxyalkyl) terephthalate. Though repolymerization may immediately follow, it is preferable that ester interchange be further performed using methanol or ethanol to obtain dimethyl terephthalate or diethyl terephthalate. Such dialkyl esters of terephthalic acid are preferable as they can be highly purified by distillation. The obtained dialkyl ester of terephthalic acid may now be polymerized.

The polyester may be produced through batch polymerization, semicontinuous polymerization or continuous polymerization.

Polyester chips may be turned into various moldings, including fibers, films, sheets and bolts, using common polyester molding methods. Products may be used in the textile, film, resin and other fields to manufacture various end products.

For instance, the common melt-spinning-drawing process may be used as a method to obtain polyester fiber. More specifically, after melting polyalkylene terephthalate by heating it above its melting point, it is discharged from small holes and solidified by blow-cooling, followed by the application of an oil solution and taking up of unstretched thread on a take-up device via a take-up roller.

The unstretched thread that has been taken up as described above is drawn through one or more pairs of heated rollers and then provided with a tensioning or relaxation heat treatment to obtain polyester fiber that has been endowed with the desired mechanical characteristics and other properties according to the intended use. In this regard, the drawing step may immediately follow the melt-spinning step without taking up the unstretched thread at the end of it, and this kind of continuous drawing is preferable from productivity and other industrial viewpoints. When performing such drawing and heat treatment, it is possible to select the draw ratio, drawing temperature and heat treatment conditions as appropriate according to the target fiber fineness, strength, extensibility, shrinking percentage, and the like.

EXAMPLES

Our polyesters and methods are described in more detail using examples below.

The following is a list of raw materials used in purification and polymerization:
  Biomass-derived ethylene glycol: Manufactured by Changchun Dacheng Industrial Group Co., Ltd. (ethylene glycol=98.138 wt %, 1,2-propanediol=5410 ppm, 1,2-butanediol=2390 ppm, 2,3-butanediol=6310 ppm, 1,4-butanediol=4510 ppm)
  Fossil resource-based ethylene glycol: Manufactured by Mitsubishi Chemical Corporation (ethylene glycol=99.989 wt %, 1,2-propanediol<15 ppm (undetectable), diethylene glycol=110 ppm)
  Terephthalic acid: High purity terephthalic acid manufactured by Mitsui Chemicals, Inc. (1,2-propanediol<15 ppm (undetectable))
  Dimethyl terephthalate: Manufactured by SK Chemical (1,2-propanediol<15 ppm (undetectable))
  Polyethylene glycol: Manufactured by Sanyo Chemical Industries Ltd. (1,2-propanediol<15 ppm (undetectable)), average molecular weight of 1000
  Sodium 5-sulfoisophthalate dimethyl ester: Manufactured by Sanyo Chemical Industries Ltd. (1,2-propanediol<15 ppm (undetectable))

All polymer characteristics and fiber physical properties cited in the examples were measured using the methods described below.

(1) Intrinsic Viscosity (IV) of Polyester (Unit dlg$^{-1}$)

Intrinsic viscosity (IV) of polyester was measured at 25° C. using ortho-chlorophenol as a solvent.

(2) Color Tone of Polymer

Using a color difference meter (SM color computer model SM-T45, manufactured by Suga Test Instruments Co., Ltd.), Hunter values (L, a and b) were measured.

(3) Thermostability Index (ΔIV)

The intrinsic viscosity of the specimen, which had been vacuum-dried in advance at 150° C. and 133 Pa or less for 20 hours, was measured (IVa). Using a melt indexer (model MX-101B, manufactured by Takara Industry Co., Ltd.), 6.0 g of the dried specimen was melt-extruded under the following setting conditions:

Load: 1000 g
    Orifice inside diameter: 2.092 mm
    Measurement distance: 25.4 mm
    Cylinder temperature×Retention time: 295° C.×60 minutes.

After retaining the polymer at 295° C.×60 minutes as mentioned above, it was extruded, collected and chipped, and chips from all stages of extrusion from start to finish were mixed together. The intrinsic viscosity (IVb) of the mixture was then measured, followed by the calculation of the thermostability index (ΔIV) as an indicator for the reduction in intrinsic viscosity during melting in accordance with the following formula:

$$\Delta IV=(IVa)-(IVb)$$

IVa: Intrinsic viscosity before melt-extrusion
IVb: Intrinsic viscosity after melt-extrusion.

(4) Diethylene Glycol (DEG) Content of Polymer

After adding 1,6-hexanediol as an internal standard substance, the polymer was decomposed at 260° C. using 2-aminoethanol as a solvent. After cooling, methanol was added, and neutralization with an acid took place, with precipitates filtered out. The filtrate was then subjected to a measurement using a gas chromatograph (GC-14B, manufactured by Shimadzu Corporation).

(5) Amount of 1,2-propanediol-derived Component Contained in Polymer

The following is a list of reagents used in the present analysis:

1,2-Propanediol (manufactured by Wako Pure Chemical Industries, Ltd., premium grade)
    1,2-Butanediol (manufactured by Tokyo Chemical Industry Co., Ltd.>99%, 1,2-Propanediol<15 ppm (undetectable))
    Aqueous ammonia (manufactured by Wako Pure Chemical Industries, Ltd., premium grade 28-30%)
    Methanol (manufactured by Wako Pure Chemical Industries, Ltd., for residual pesticide-PCB testing, 1,2-propanediol<15 ppm (undetectable))
    Terephthalic acid (manufactured by Wako Pure Chemical Industries, Ltd., grade 1, 1,2-propanediol<15 ppm (undetectable))
    Purified water (prepared using Milli-Q Integral 3, manufactured by Millipore).

First, an aqueous solution containing 1,2-butanediol by 1490 μg/ml was prepared for use as an internal standard solution A. Next, 0.1 g of the specimen was weighed and placed in a vial, and 0.015 ml of the internal standard solution A and 1 ml of aqueous ammonia were added. After sealing the vial with a stopper, it was heated for 3 hours at 150° C. and then left to stand to cool down to room temperature. After this, 2 ml of methanol and 2.0 g of terephthalic acid were added, followed by 15 minutes of shaking and 3 minutes of centrifugal separation at 4000 G. The supernatant liquid was taken out and subjected to a measurement using a gas chromatograph (5890 series II, manufactured by Hewlett Packard, injector: split/splitless, detector: hydrogen flame ionization detector) under the setting conditions specified below, with the content of the 1,2-propanediol-derived component determined using a calibration curve to be describe later:

Injector temperature: 220° C.
    Column head pressure: 20 psi
    Carrier gas: Helium
    Sample injection method: Split (linear flow rate 25 ml/min)
    Septum purge: Helium 3.0 ml/min
    Amount of sample introduced: 1.0 μl
    Detector temperature: 220° C.
    Gas flow rate: Hydrogen 40 ml/min, air 400 ml/min and nitrogen 40 ml/min
    Oven heating starting temperature: 60° C. (retention time 2 minutes)
    Oven heating stopping temperature: 220° C. (retention time 30 seconds)
    Oven heating rate: 20° C./min (slope of straight line graph).

The calibration curve for 1,2-propanediol was prepared in the following procedure: An aqueous solution containing 2500 μg/ml of 1,2-propanediol was prepared for use as a standard mother liquid B. Next, 0.003 to 0.08 ml of the standard mother liquid B and 0.025 ml of the internal standard solution A were placed in a 5 ml measuring flask and diluted with a constant volume of a mixed solvent (methanol:purified water=2:1, containing ethylene glycol by 1.1%) to prepare seven types of standard solution C containing varying amounts of the standard mother liquid B. Each type of standard solution C was subjected to a measurement using a gas chromatograph under the conditions specified above, and a calibration curve for 1,2-propanediol was produced by plotting the peak area ratio between the obtained 1,2-propanediol and the internal standard substance and the concentration ratio between the 1,2-propanediol and the internal standard substance contained in the standard solution C.

The accuracy of the present analysis was verified using the method described below. First, an aqueous solution containing 2500 μg/ml of 1,2-propanediol was prepared for use as a standard solution D. Next, 0.1 g of the specimen was weighed and placed in a vial, and 0.01 ml of the standard solution D, 0.015 ml of the internal standard solution A and 1 ml of aqueous ammonia were added. After sealing the vial with a stopper, it was heated for 3 hours at 150° C. and then left to stand to cool down to room temperature. After this, 2 ml of methanol and 2.0 g of terephthalic acid were added, followed by 15 minutes of shaking and 3 minutes of centrifugal separation at 4000 G. The supernatant liquid was taken out and subjected to a measurement using a gas chromatograph (5890 series II, manufactured by Hewlett Packard) under the setting conditions specified above. The content of the 1,2-propanediol-derived component was then determined using the calibration curve described above, with the recovery rate of standard addition for 1,2-propanediol found to be 105%.

(6) Amount of 1,2-propanediol Contained in Ethylene Glycol

The following is a list of reagents used in the present analysis:

1,2-Propanediol (manufactured by Wako Pure Chemical Industries, Ltd., premium grade)
    Acetone (manufactured by Wako Pure Chemical Industries, Ltd., for residual pesticide-PCB testing, 1,2-propanediol<15 ppm (undetectable)).

About 0.15 g of ethylene glycol was weighed and dissolved/diluted with a constant volume of acetone in a 5 ml measuring flask. The prepared solution was subjected to a measurement using a gas chromatograph (5890 series II, manufactured by Hewlett Packard, injector: split/splitless, detector: hydrogen flame ionization detector) under the setting conditions specified below, with the 1,2-propanediol content determined using a calibration curve obtained from the same measurement procedure performed on 1,2-propanediol in place of the specimen:

Injector temperature: 250° C.
Column head pressure: 15 psi
Carrier gas: Helium
Sample injection method: Split (linear flow rate 50 ml/min)
Septum purge: Helium 3.0 ml/min
Amount of sample introduced: 1.0 μl
Detector temperature: 250° C.
Gas flow rate: Hydrogen 40 ml/min, air 400 ml/min and nitrogen 40 ml/min
Oven heating starting temperature: 50° C. (retention time 3 minutes)
Oven heating stopping temperature: 250° C. (retention time 1 minute)
Oven heating rate: 15° C./min (slope of straight line graph).

(7) Accumulation of Deposits on Spinneret Area and Frequency of Broken Thread

Using a long-focus microscope, the spinneret area was observed 120 hours after the start of the spinning of polyester fiber (with 1 ton of fiber spun) for any accumulation of deposits. The condition of the spinneret area was assessed according to the following grades: Few deposits observed and no broken thread occurring ⊚ (pass/good); Deposits observed and broken thread occurring at least once×(failure).

(8) Strength and Elongation

Using a "Tensilon" tensile tester manufactured by Toyo Baldwin Co., Ltd., an S—S curve of a 25 cm-long specimen was obtained at a tension speed of 30 cm/min, and the strength and elongation of the drawn polyester yarn was calculated.

(9) Biobased Content Measurement Method

The biobased content of the polyester was determined in accordance with ASTM D6866.

Namely, after pulverizing a specimen with sandpaper and a grinder, it was heated with copper oxide and completely oxidized to carbon dioxide, followed by reduction to graphite with iron powder and conversion into a single compound of carbon. The obtained graphite sample was introduced into an AMS system and the $^{14}C$ concentration was measured. At the same time, the $^{14}C$ concentration of oxalic acid, a standard substance (supplied by National Institute of Standards and Technology, NIST), was measured. Next, $\Delta^{14}C$ was calculated using the following formula:

$$\Delta^{14}C = \{(^{14}As - ^{14}Ar)/^{14}Ar\} \times 1000$$

where $^{14}As$ is the ratio between $^{14}C$ and $^{12}C$ ($^{14}C/^{12}C$) of the specimen, and $^{14}Ar$ is the ratio between $^{14}C$ and $^{12}C$ ($^{14}C/^{12}C$) of the standard substance.

Based on this $\Delta^{14}C$ value, pMC(percent Modern Carbon) was then calculated using the following formula:

$$pMC = \Delta^{14}C/10 + 100.$$

Finally, the biobased content was calculated by multiplying the pMC value by 0.95 (=100/105) in accordance with ASTM (American Society for Testing and Materials) D6866 as follows:

Biobased content (%)=0.95×pMC.

Reference Example 1

The acquired 20 kg of biomass-derived ethylene glycol (manufactured by Changchun Dacheng Industrial Group Co., Ltd.) was subjected to a distillation operation, performed under a set of conditions comprising 40 theoretical plates, a pressure of 50 mmHg and a reflux ratio of 10, and crude ethylene glycol was obtained as bottom residual. This crude ethylene glycol contained 3510 ppm of 1,2-propanediol. The obtained crude ethylene glycol was heated for 15 hours in a heating pot set to a temperature of 190° C., followed by cooling down to room temperature.

Meanwhile, activated carbon (Taiko SGA, manufactured by Futamura Chemical Industries Co., Ltd.) was washed with soft water and dried, and then packed in an activated carbon treatment system. The activated carbon layer was 300 cm thick, and the crude ethylene glycol, which had been heated and cooled as described above, was passed through it at a space velocity of 0.57 $hr^{-1}$ and recovered. In the end, biomass-derived ethylene glycol (purified product) containing 220 ppm of 1,2-propanediol was obtained.

Reference Example 2

Following the same procedure as Reference Example 1, except that the thickness of the activated carbon layer and the space velocity were changed to 200 cm and 0.86 $hr^{-1}$, respectively, biomass-derived ethylene glycol (purified product) containing 900 ppm of 1,2-propanediol was obtained.

Reference Example 3

Following the same procedure as Reference Example 1, except that the heating time of crude ethylene glycol after the distillation operation, the thickness of the activated carbon layer and the space velocity were changed to 30 hours, 500 cm and 0.34 $hr^{-1}$, respectively, biomass-derived ethylene glycol (purified product) containing 50 ppm of 1,2-propanediol was obtained.

Reference Example 4

The biomass-derived ethylene glycol (manufactured by Changchun Dacheng Industrial Group Co., Ltd.) was heated for 10 hours in a heating pot set to a temperature of 190° C., followed by cooling down to room temperature.

Meanwhile, activated carbon was washed with soft water and dried, and then packed in an activated carbon treatment system. The activated carbon layer was 150 cm thick, and the biomass-derived ethylene glycol, which had been heated and cooled as described above, was passed through it at a space velocity of 1.14 $hr^{-1}$ and recovered. In the end, biomass-derived ethylene glycol (crude product) containing 2780 ppm of 1,2-propanediol was obtained.

Reference Example 5

The acquired 20 kg of biomass-derived ethylene glycol (manufactured by Changchun Dacheng Industrial Group Co., Ltd.) was subjected to a first distillation operation, performed under a set of conditions comprising 30 theoretical plates, a pressure of 50 mmHg and a reflux ratio of 5, and crude ethylene glycol was obtained as bottom residual. This crude ethylene glycol, which contained 4190 ppm of 1,2-propanediol, was then subjected to a second distillation operation, performed under a set of conditions comprising 30 theoretical plates, a pressure of 50 mmHg, and a reflux ratio of 5. In the end, biomass-derived ethylene glycol (crude product) containing 3030 ppm of 1,2-propanediol was obtained as bottom residual.

Reference Example 6

Fossil resource-based ethylene glycol with an undetectable 1,2-propanediol content (less than 15 ppm) (manufactured by Mitsubishi Chemical Corporation) was used as the ethylene glycol for Reference Example 6.

Manufacturing Example 1

A quantity of magnesium acetate equivalent, on a magnesium atom basis, to 60 ppm with respect to the polymer to be obtained, 100 kg of dimethyl terephthalate and 58 kg of ethylene glycol were dissolved at 150° C. in a nitrogen atmosphere and then heated to 230° C. over 3 hours, while being stirred, to distil the methanol out and have an ester interchange reaction progress, with bis(hydroxyethyl)terephthalate obtained in the process.

Working Example 1

Throughout this working example, the biomass-derived ethylene glycol (purified product) obtained in Reference Example 1 was used.

First, approx. 100 kg of bis(hydroxyethyl)terephthalate, produced in Manufacturing Example 1 using the biomass-derived ethylene glycol (purified product) obtained in Reference Example 1, was transferred to the condensation polymerization tank. A quantity of antimony trioxide, equivalent, on an antimony atom basis, to 250 ppm, and a quantity of trimethyl phosphate, equivalent, on a phosphorus atom basis, to 50 ppm—both with respect to the polymer to be obtained—were mixed in a mixing tank 30 minutes before their introduction to the condensation polymerization tank. After being stirred for 30 minutes at room temperature, the mixture was added to the bis(hydroxyethyl)terephthalate in the condensation polymerization tank. Five minutes later, a quantity of an ethylene glycol slurry of titanium oxide particles, equivalent, on a titanium oxide particle basis, to 0.1 wt % with respect to the polymer to be obtained, was also added. Five minutes later, the pressure of the reaction system was reduced to start the reaction. As the interior temperature of the reaction vessel was gradually increased from 250° C. to 280° C., the pressure was reduced to 110 Pa. Both the final temperature and final pressure were set to be reached in 60 minutes. As soon as the predetermined stirring torque was reached, the condensation polymerization reaction was stopped by returning the reaction system to normal pressure via a nitrogen purge, and the polymer was discharged in strand form and cooled, and this was immediately followed by cutting to obtain polymer pellets. It took 3 hours and 5 minutes from the start of pressure reduction to the reaching of the predetermined stirring torque. The obtained polymer was good in terms of color tone and thermostability. The polymer characteristics are summarized in Table 3.

The types of the biomass-derived ethylene glycol and the dicarboxylic acid component and types and blending amounts of the copolymerization components and esterification or ester interchange catalyst are summarized in Table 1. The types and blending amounts of the catalyst, phosphorus compound and other additives added to the condensation polymerization tank, as well as the blending amount of titanium oxide particles, are summarized in Table 2.

Working Example 2

Throughout this working example, the biomass-derived ethylene glycol (purified product) obtained in Reference Example 1 was used.

Over 4 hours, a slurry of 82.5 kilograms of terephthalic acid and 35.4 kg of ethylene glycol was gradually fed to an esterification reaction tank in which approx. 100 kg of bis(hydroxyethyl)terephthalate, produced in Manufacturing Example 1 using the biomass-derived ethylene glycol (purified product) obtained in Reference Example 1, had been placed and which had been kept at a temperature of 250° C. and pressure of 1.2×100,000 Pa. Even after the feeding was completed, the esterification reaction was allowed to continue for 1 hour, and the obtained 101.5 kg of an esterification reaction product was transferred to the condensation polymerization tank.

After transfer, a quantity of antimony trioxide, equivalent, on an antimony atom basis, to 250 ppm, and a quantity of trimethyl phosphate, equivalent, on a phosphorus atom basis, to 20 ppm—both with respect to the polymer to be obtained—were, as an ethylene glycol solution, added to the esterification reaction product. Five minutes later, a quantity of an ethylene glycol slurry of titanium oxide particles, equivalent, on a titanium oxide particle basis, to 0.1 wt % with respect to the polymer to be obtained, was also added. After this, the reaction was started by reducing the pressure, while stirring at 30 rpm. As the interior temperature of the reaction vessel was gradually increased from 250° C. to 280° C., the pressure was reduced to 110 Pa. Both the final temperature and final pressure were set to be reached in 60 minutes. As soon as the predetermined stirring torque was reached, the condensation polymerization reaction was stopped by returning the reaction system to normal pressure via a nitrogen purge, and the polymer was discharged in strand form and cooled, and this was immediately followed by cutting to obtain polymer pellets. It took exactly 3 hours from the start of pressure reduction to the reaching of the predetermined stirring torque. The obtained polymer was good in terms of color tone and thermostability. The polymer characteristics are summarized in Table 3.

Working Examples 3 and 4

Polymer pellets were obtained in the same manner as Manufacturing Example 1 and Working Example 2, except that the ethylene glycol used was changed as specified in Table 1. Evaluation results for the obtained polymer pellets are summarized in Table 3.

Working Example 5

Polymer pellets were obtained in the same manner as Working Example 1, except that 1.0 kg of polyethylene glycol with an average molecular weight of 1000 was placed at the same time that 100 kg of dimethyl terephthalate and 58 kg of ethylene glycol were placed. Results are summarized in Table 3.

Working Example 6

Polymer pellets were obtained in the same manner as Working Example 2, except that a quantity of polyethylene glycol with an average molecular weight of 1000, equivalent to 1 wt % with respect to the weight of the polymer to be obtained, was added to the esterification reactant. Results are summarized in Table 3.

Working Example 7

Polymer pellets were obtained in the same manner as Working Example 2, except that a quantity of polyethylene glycol with an average molecular weight of 1000, equivalent to 8 wt % with respect to the weight of the polymer to be obtained, was added to the esterification reactant. Results are summarized in Table 3.

Working Examples 8 and 9

Polymer pellets were obtained in the same manner as Working Example 6, except that the ethylene glycol used was changed as specified in Table 1. Results are summarized in Table 3.

Working Example 10

Polymer pellets were obtained in the same manner as Working Example 1, except that 1.5 kg of sodium 5-sulfoisophthalate dimethyl ester was placed at the same time that 100 kg of dimethyl terephthalate and 58 kg of ethylene glycol were placed. Results are summarized in Table 3.

Working Example 11

Polymer pellets were obtained in the same manner as Working Example 2, except that a quantity of sodium 5-sulfoisophthalate dimethyl ester, equivalent to 1 mol % with reference to the total dicarboxylic acid component as the main ingredient of the polymer to be obtained, was added to the esterification reactant. Results are summarized in Table 3.

Working Example 12

Polymer pellets were obtained in the same manner as Working Example 2, except that a quantity of sodium 5-sulfoisophthalate dimethyl ester, equivalent to 8 mol % with reference to the total dicarboxylic acid component as the main ingredient of the polymer to be obtained, was added to the esterification reactant. Results are summarized in Table 3.

Working Examples 13 and 14

Polymer pellets were obtained in the same manner as Working Example 11, except that the ethylene glycol used was changed as specified in Table 1. Results are summarized in Table 3.

Working Example 15

Polymer pellets were obtained in the same manner as Working Example 1, except that 1.0 kg of polyethylene glycol with an average molecular weight of 1000 and 3.0 kg of sodium 5-sulfoisophthalate dimethyl ester was placed at the same time that 100 kg of dimethyl terephthalate and 58 kg of ethylene glycol were placed. Results are summarized in Table 3.

Working Example 16

Polymer pellets were obtained in the same manner as Working Example 2, except that a quantity of polyethylene glycol with an average molecular weight of 1000, equivalent to 1 wt % with respect to the weight of the polymer to be obtained, and a quantity of sodium 5-sulfoisophthalate dimethyl ester, equivalent to 2 mol % with reference to the total dicarboxylic acid component as the main ingredient of the polymer to be obtained, were added to the esterification reactant. Results are summarized in Table 3.

Working Examples 17 and 18

Polymer pellets were obtained in the same manner as Working Example 16, except that the ethylene glycol used was changed as specified in Table 1. Results are summarized in Table 3.

Working Examples 19 to 26

Polymer pellets were obtained in the same manner as Working Example 16, except that the type and blending amount of the phosphorus compound added, type and blending amount of the polymerization catalyst used, types and blending amounts of other additives and blending amount of titanium oxide particles were changed as specified in Table 2. Results are summarized in Table 3.

TABLE 1

| | Biomass-derived EG Type | Dicarboxylic acid component Type | Copolymerization components | | Catalyst 1 Esterification or ester interchange catalyst | |
|---|---|---|---|---|---|---|
| | | | Polyethylene glycol wt % (vs. PET) | Sodium 5-sulfoisophthalate mol % (vs. total dicarboxylic acid component) | Type | Blending amount (ppm) (equivalent, atom basis) |
| Working Example 1 | Reference Example 1 | DMT | — | — | MGA | 60 |
| Working Example 2 | Reference Example 1 | TPA | — | — | — | — |
| Working Example 3 | Reference Example 2 | TPA | — | — | — | — |
| Working Example 4 | Reference Example 3 | TPA | — | — | — | — |
| Working Example 5 | Reference Example 1 | DMT | 1 | — | MGA | 60 |
| Working Example 6 | Reference Example 1 | TPA | 1 | — | — | — |
| Working Example 7 | Reference Example 1 | TPA | 8 | — | — | — |

TABLE 1-continued

|  | Biomass-derived EG Type | Dicarboxylic acid component Type | Copolymerization components Polyethylene glycol wt % (vs. PET) | Copolymerization components Sodium 5-sulfoisophthalate mol % (vs. total dicarboxylic acid component) | Catalyst 1 Esterification or ester interchange catalyst Type | Catalyst 1 Esterification or ester interchange catalyst Blending amount (ppm) (equivalent, atom basis) |
|---|---|---|---|---|---|---|
| Working Example 8 | Reference Example 2 | TPA | 1 | — | — | — |
| Working Example 9 | Reference Example 3 | TPA | 1 | — | — | — |
| Working Example 10 | Reference Example 1 | DMT | — | 1 | MGA | 60 |
| Working Example 11 | Reference Example 1 | TPA | — | 1 | — | — |
| Working Example 12 | Reference Example 1 | TPA | — | 8 | — | — |
| Working Example 13 | Reference Example 2 | TPA | — | 1 | — | — |
| Working Example 14 | Reference Example 3 | TPA | — | 1 | — | — |
| Working Example 15 | Reference Example 1 | DMT | 1 | 2 | MGA | 60 |
| Working Example 16 | Reference Example 1 | TPA | 1 | 2 | — | — |
| Working Example 17 | Reference Example 2 | TPA | 1 | 2 | — | — |
| Working Example 18 | Reference Example 3 | TPA | 1 | 2 | — | — |
| Working Example 19 | Reference Example 1 | TPA | 1 | 2 | — | — |
| Working Example 20 | Reference Example 1 | TPA | 1 | 2 | — | — |
| Working Example 21 | Reference Example 1 | TPA | 1 | 2 | — | — |
| Working Example 22 | Reference Example 1 | TPA | 1 | 2 | — | — |
| Working Example 23 | Reference Example 1 | TPA | 1 | 2 | — | — |
| Working Example 24 | Reference Example 1 | TPA | 1 | 2 | — | — |
| Working Example 25 | Reference Example 1 | TPA | 1 | 2 | — | — |
| Working Example 26 | Reference Example 1 | TPA | 1 | 2 | — | — |

EG: Ethylene glycol
TPA: Terephthalic acid
DMT: Dimethyl terephthalate
MGA: Magnesium acetate

TABLE 2

|  | Catalyst 2 Polymerization catalyst Type | Catalyst 2 Polymerization catalyst Blending amount (ppm) (equivalent, atom basis) | Additives Phosphorus compound Type | Additives Phosphorus compound Blending amount (ppm) (equivalent, atom basis) | Additives Other additive Type | Additives Other additive Blending amount (ppm) (equivalent, atom basis) | $TiO_2$ Blending amount (wt %) |
|---|---|---|---|---|---|---|---|
| Working Example 1 | $Sb_2O_3$ | 250 | TMPA | 50 | — | — | 0.1 |
| Working Example 2 | $Sb_2O_3$ | 250 | TMPA | 20 | — | — | 0.1 |
| Working Example 3 | $Sb_2O_3$ | 250 | TMPA | 20 | — | — | 0.1 |
| Working Example 4 | $Sb_2O_3$ | 250 | TMPA | 20 | — | — | 0.1 |
| Working Example 5 | $Sb_2O_3$ | 250 | TMPA | 50 | — | — | 0.1 |
| Working Example 6 | $Sb_2O_3$ | 250 | TMPA | 20 | — | — | 0.1 |

TABLE 2-continued

|  | Catalyst 2 Polymerization catalyst | | Additives | | | | |
|---|---|---|---|---|---|---|---|
|  |  |  | Phosphorus compound | | Other additive | | |
|  | Type | Blending amount (ppm) (equivalent, atom basis) | Type | Blending amount (ppm) (equivalent, atom basis) | Type | Blending amount (ppm) (equivalent, atom basis) | TiO$_2$ Blending amount (wt %) |
|---|---|---|---|---|---|---|---|
| Working Example 7 | Sb$_2$O$_3$ | 250 | TMPA | 20 | — | — | 0.1 |
| Working Example 8 | Sb$_2$O$_3$ | 250 | TMPA | 20 | — | — | 0.1 |
| Working Example 9 | Sb$_2$O$_3$ | 250 | TMPA | 20 | — | — | 0.1 |
| Working Example 10 | Sb$_2$O$_3$ | 250 | TMPA | 50 | — | — | 0.1 |
| Working Example 11 | Sb$_2$O$_3$ | 250 | TMPA | 20 | — | — | 0.1 |
| Working Example 12 | Sb$_2$O$_3$ | 250 | TMPA | 20 | — | — | 0.1 |
| Working Example 13 | Sb$_2$O$_3$ | 250 | TMPA | 20 | — | — | 0.1 |
| Working Example 14 | Sb$_2$O$_3$ | 250 | TMPA | 20 | — | — | 0.1 |
| Working Example 15 | Sb$_2$O$_3$ | 250 | TMPA | 50 | — | — | 0.1 |
| Working Example 16 | Sb$_2$O$_3$ | 250 | TMPA | 20 | — | — | 0.1 |
| Working Example 17 | Sb$_2$O$_3$ | 250 | TMPA | 20 | — | — | 0.1 |
| Working Example 18 | Sb$_2$O$_3$ | 250 | TMPA | 20 | — | — | 0.1 |
| Working Example 19 | Sb$_2$O$_3$ | 250 | PA | 20 | — | — | 0.1 |
| Working Example 20 | Citric acid Ti | 5 | TMPA | 25 | MGA | 30 | 0.1 |
| Working Example 21 | Mannitol Ti | 5 | TMPA | 25 | MGA | 30 | 0.1 |
| Working Example 22 | Basic Aluminium Acetate | 20 | TMPA | 25 | MGA | 30 | 0.1 |
| Working Example 23 | Mannitol Ti | 5 | PA | 25 | MGA | 30 | 0.1 |
| Working Example 24 | Mannitol Ti | 5 | PEP36 | 25 | MGA | 30 | 0.1 |
| Working Example 25 | Mannitol Ti | 5 | GSY | 25 | MGA | 30 | 0.1 |
| Working Example 26 | Sb$_2$O$_3$ | 250 | TMPA | 20 | — | — | 0 |

Sb$_2$O$_3$: Antimony trioxide
TMPA: Trimethyl phosphate
Citric acid Ti: Citric acid chelate titanium complex
PA: Phosphoric acid
Mannitol Ti: Mannitol chelate titanium complex
TiO$_2$: Titanium oxide
PEP36: 3,9-Bis(2,6-di-t-butyl-4-methylphenoxy)-2,4,8,10-tetraoxa-3,9-diphosphaspiro[5,5]undecane (manufactured by ADEKA CORPORATION)
GSY: Tetrakis(2,4-di-t-butyl-5-methylphenyl)[1,1-biphenyl]-4,4'-diylbisphosphonite (manufactured by Osaki Industry Co., Ltd.)

TABLE 3

|  | Polymer characteristics | | | | | | | | |
|---|---|---|---|---|---|---|---|---|---|
|  | Polymerization time | Intrinsic viscosity | | Color tone | | | DEG content | Content of 1,2-PD-derived components | Biobased Content |
|  | (hr:min) | IV [dl/g] | ΔIV [dl/g] | L value | a value | b value | [wt %] | [ppm] | [%] |
| Working Example 1 | 3:05 | 0.664 | 0.054 | 64 | −4.3 | 3 | 1.5 | 51 | 20 |
| Working Example 2 | 3:00 | 0.668 | 0.059 | 66 | −2.3 | 2 | 1.2 | 50 | 20 |
| Working Example 3 | 3:03 | 0.663 | 0.058 | 66 | −2.4 | 2 | 1.5 | 203 | 20 |
| Working Example 4 | 3:05 | 0.667 | 0.051 | 66 | −2.6 | 2 | 1.4 | 15 | 20 |

TABLE 3-continued

|  | Polymerization time (hr:min) | Intrinsic viscosity | | Color tone | | | DEG content [wt %] | Content of 1,2-PD-derived components [ppm] | Biobased Content [%] |
| --- | --- | --- | --- | --- | --- | --- | --- | --- | --- |
|  |  | IV [dl/g] | ΔIV [dl/g] | L value | a value | b value |  |  |  |
| Working Example 5 | 3:14 | 0.701 | 0.064 | 64 | −4.6 | 10 | 1.5 | 53 | 20 |
| Working Example 6 | 3:11 | 0.705 | 0.063 | 64 | −2.4 | 9 | 1.7 | 49 | 20 |
| Working Example 7 | 2:50 | 0.752 | 0.066 | 66 | −3.1 | 12 | 1.6 | 44 | 18 |
| Working Example 8 | 3:15 | 0.702 | 0.061 | 62 | −2.6 | 9 | 1.3 | 198 | 20 |
| Working Example 9 | 3:17 | 0.701 | 0.064 | 63 | −2.3 | 9 | 1.6 | 16 | 20 |
| Working Example 10 | 3:02 | 0.622 | 0.068 | 66 | −4.5 | 11 | 2.1 | 51 | 20 |
| Working Example 11 | 3:03 | 0.623 | 0.066 | 66 | −2.8 | 9 | 2.1 | 49 | 20 |
| Working Example 12 | 2:53 | 0.501 | 0.069 | 69 | −3.5 | 15 | 2.8 | 43 | 20 |
| Working Example 13 | 3:04 | 0.626 | 0.063 | 66 | −2.3 | 9 | 2.3 | 202 | 20 |
| Working Example 14 | 3:01 | 0.621 | 0.068 | 66 | −2.6 | 9 | 2.2 | 15 | 20 |
| Working Example 15 | 3:00 | 0.693 | 0.068 | 66 | −4.6 | 12 | 2.2 | 50 | 20 |
| Working Example 16 | 3:04 | 0.694 | 0.064 | 66 | −2.8 | 10 | 2.2 | 51 | 20 |
| Working Example 17 | 3:03 | 0.693 | 0.062 | 66 | −2.7 | 11 | 2.1 | 200 | 20 |
| Working Example 18 | 3:06 | 0.697 | 0.067 | 66 | −2.8 | 10 | 2.2 | 15 | 20 |
| Working Example 19 | 3:00 | 0.694 | 0.064 | 66 | −2.4 | 10 | 2.3 | 48 | 20 |
| Working Example 20 | 3:01 | 0.695 | 0.069 | 69 | −5.6 | 15 | 2.1 | 53 | 20 |
| Working Example 21 | 3:03 | 0.692 | 0.068 | 69 | −5.1 | 12 | 2.2 | 54 | 20 |
| Working Example 22 | 3:05 | 0.698 | 0.065 | 64 | −3.8 | 11 | 2.4 | 50 | 20 |
| Working Example 23 | 3:07 | 0.696 | 0.067 | 69 | −4.8 | 12 | 2 2 | 51 | 20 |
| Working Example 24 | 3:01 | 0.692 | 0.063 | 69 | −3.9 | 12 | 2 2 | 50 | 20 |
| Working Example 25 | 3:02 | 0.696 | 0.069 | 69 | −3.5 | 12 | 2.1 | 49 | 20 |
| Working Example 26 | 3:03 | 0.697 | 0.066 | 56 | −1.5 | 9 | 2.3 | 52 | 20 |

DEG: Diethylene glycol
1,2-PD: 1,2-Propanediol
1,2-PD detection limit: 15 ppm

Working Example 27

The polyethylene terephthalate pellets obtained in Working Example 1 were vacuum-dried at 150° C. for 12 hours and then melted at a spinning temperature of 285° C. After this, the molten polyethylene terephthalate was discharged from a spinneret featuring 36 small holes, each 0.18 mm in diameter, and taken up on a take-up device at a circumferential speed of 1000 m/min to obtain unstretched thread. During this process, the accumulation of some deposits was observed on the spinneret area, but hardly any broken thread incidents occurred, with virtually no noticeable rise in filtration pressure. The obtained unstretched thread was subjected to a drawing-heat treatment at a drawing temperature of 90° C., a heat treatment temperature 140° C. and a draw ratio of 3.0 using a hot-roll drawing machine to obtain drawn thread. Measurement results for the accumulation of deposits on the spinneret area, frequency of broken thread, and strength and elongation of the drawn thread are summarized in Table 4.

Working Examples 28 to 52

The polyethylene terephthalate pellets obtained in Working Examples 2 to 26 were subjected to spinning and drawing in the same manner as Working Example 27. During this process, hardly any accumulation of deposits was observed on the spinneret area, and no broken thread incidents occurred. Results are summarized in Table 4.

TABLE 4

| | Input polymer No. of corresponding working example | Accumulation of deposits on spinneret area and frequency of broken thread | Strength (cN/dtex) | Elongation (%) |
|---|---|---|---|---|
| Working Example 27 | 1 | ◎ | 4.1 | 38 |
| Working Example 28 | 2 | ◎ | 4.1 | 38 |
| Working Example 29 | 3 | ◎ | 4.1 | 38 |
| Working Example 30 | 4 | ◎ | 4.1 | 38 |
| Working Example 31 | 5 | ◎ | 3.8 | 40 |
| Working Example 32 | 6 | ◎ | 3.7 | 40 |
| Working Example 33 | 7 | ◎ | 2.8 | 25 |
| Working Example 34 | 8 | ◎ | 3.7 | 40 |
| Working Example 35 | 9 | ◎ | 3.7 | 40 |
| Working Example 36 | 10 | ◎ | 3.7 | 40 |
| Working Example 37 | 11 | ◎ | 3.7 | 40 |
| Working Example 38 | 12 | ◎ | 2.1 | 25 |
| Working Example 39 | 13 | ◎ | 3.7 | 40 |
| Working Example 40 | 14 | ◎ | 3.7 | 40 |
| Working Example 41 | 15 | ◎ | 3.6 | 40 |
| Working Example 42 | 16 | ◎ | 3.6 | 40 |
| Working Example 43 | 17 | ◎ | 3.6 | 40 |
| Working Example 44 | 18 | ◎ | 3.6 | 40 |
| Working Example 45 | 19 | ◎ | 3.6 | 40 |
| Working Example 46 | 20 | ◎ | 3.6 | 40 |
| Working Example 47 | 21 | ◎ | 3.6 | 40 |
| Working Example 48 | 22 | ◎ | 3.6 | 40 |
| Working Example 49 | 23 | ◎ | 3.6 | 40 |
| Working Example 50 | 24 | ◎ | 3.6 | 40 |
| Working Example 51 | 25 | ◎ | 3.6 | 40 |
| Working Example 52 | 26 | ◎ | 3.6 | 40 |

With regard to Comparative Examples 1 to 30 below, the types of ethylene glycol and dicarboxylic acid components, and type and blending amount of copolymerization components and the esterification or ester interchange catalyst are summarized in Table 5. The types and blending amounts of the polymerization catalyst, phosphorus compound and other additives added to the condensation polymerization tank, as well as the blending amount of titanium oxide particles, are summarized in Table 6.

Comparative Examples 1 and 2

Polymer pellets were obtained in the same manner as Working Example 1, except that the ethylene glycol used was changed as specified in Table 5. Evaluation results for the obtained polymer pellets are summarized in Table 7.

Comparative Examples 3 to 5

Polymer pellets were obtained in the same manner as Working Example 2, except that the ethylene glycol used was changed as specified in Table 5. Results are summarized in Table 7.

Comparative Examples 6 and 7

Polymer pellets were obtained in the same manner as Working Example 5, except that the ethylene glycol used was changed as specified in Table 5. Results are summarized in Table 7.

Comparative Examples 8, 10 and 11

Polymer pellets were obtained in the same manner as Working Example 6, except that the ethylene glycol used was changed as specified in Table 5. Results are summarized in Table 7.

Comparative Example 9

Polymer pellets were obtained in the same manner as Comparative Example 8, except that a quantity of polyethylene glycol with an average molecular weight of 1000, equivalent to 8 wt % with respect to the weight of the polymer to be obtained, was added to the esterification reactant. Results are summarized in Table 7.

Comparative Examples 12 and 13

Polymer pellets were obtained in the same manner as Working Example 10, except that the ethylene glycol used was changed as specified in Table 5. Results are summarized in Table 7.

Comparative Examples 14, 16 and 17

Polymer pellets were obtained in the same manner as Working Example 11, except that the ethylene glycol used was changed as specified in Table 5. Results are summarized in Table 7.

Comparative Example 15

Polymer pellets were obtained in the same manner as Comparative Example 14, except that a quantity of sodium 5-sulfoisophthalate dimethyl ester, equivalent to 8 mol % with reference to the total dicarboxylic acid component as the main ingredient of the polymer to be obtained, was added to the esterification reactant. Results are summarized in Table 7.

Comparative Examples 18 and 19

Polymer pellets were obtained in the same manner as Working Example 15, except that the ethylene glycol used was changed as specified in Table 5. Results are summarized in Table 7.

Comparative Examples 20 to 22

Polymer pellets were obtained in the same manner as Working Example 16, except that the ethylene glycol used was changed as specified in Table 5. Results are summarized in Table 7.

Comparative Examples 23 to 30

Polymer pellets were obtained in the same manner as Comparative Example 22, except that the type and blending amount of the phosphorus compound added, type and blending amount of the polymerization catalyst, types and blending amounts of other additives and blending amount of titanium oxide were changed as specified in Table 6. Results are summarized in Table 7.

TABLE 5

|  | EG | | Dicarboxylic acid component Type | Copolymerization components | | Catalyst 1 | |
|---|---|---|---|---|---|---|---|
|  | | | | | Sodium 5-sulfoisophthalate | Esterification or ester interchange catalyst | |
|  | Biomass-derived Type | Fossil resource-based Type |  | Polyethylene glycol wt % (vs. PET) | mol % (vs. total dicarboxylic acid component) | Type | Blending amount (ppm) (equivalent, atom basis) |
| Comparative Example 1 | Reference Example 4 | — | DMT | — | — | MGA | 60 |
| Comparative Example 2 | — | Reference Example 6 | DMT | — | — | MGA | 60 |
| Comparative Example 3 | Reference Example 4 | — | TPA | — | — | — | — |
| Comparative Example 4 | Reference Example 5 | — | TPA | — | — | — | — |
| Comparative Example 5 | — | Reference Example 6 | TPA | — | — | — | — |
| Comparative Example 6 | Reference Example 4 | — | DMT | 1 | — | MGA | 60 |
| Comparative Example 7 | — | Reference Example 6 | DMT | 1 | — | MGA | 60 |
| Comparative Example 8 | Reference Example 4 | — | TPA | 1 | — | — | — |
| Comparative Example 9 | Reference Example 4 | — | TPA | 8 | — | — | — |
| Comparative Example 10 | Reference Example 5 | — | TPA | 1 | — | — | — |
| Comparative Example 11 | — | Reference Example 6 | TPA | 1 | — | — | — |
| Comparative Example 12 | Reference Example 4 | — | DMT | — | 1 | MGA | 60 |
| Comparative Example 13 | — | Reference Example 6 | DMT | — | 1 | MGA | 60 |
| Comparative Example 14 | Reference Example 4 | — | TPA | — | 1 | — | — |
| Comparative Example 15 | Reference Example 4 | — | TPA | — | 8 | — | — |
| Comparative Example 16 | Reference Example 5 | — | TPA | — | 1 | — | — |
| Comparative Example 17 | — | Reference Example 6 | TPA | — | 1 | — | — |
| Comparative Example 18 | Reference Example 4 | — | DMT | 1 | 2 | MGA | 60 |
| Comparative Example 19 | — | Reference Example 6 | DMT | 1 | 2 | MGA | 60 |
| Comparative Example 20 | Reference Example 4 | — | TPA | 1 | 2 | — | — |
| Comparative Example 21 | Reference Example 5 | — | TPA | 1 | 2 | — | — |
| Comparative Example 22 | — | Reference Example 6 | TPA | 1 | 2 | — | — |
| Comparative Example 23 | — | Reference Example 6 | TPA | 1 | 2 | — | — |
| Comparative Example 24 | — | Reference Example 6 | TPA | 1 | 2 | — | — |
| Comparative Example 25 | — | Reference Example 6 | TPA | 1 | 2 | — | — |

TABLE 5-continued

| | EG | | | Copolymerization components | | Catalyst 1 | |
|---|---|---|---|---|---|---|---|
| | | | | Polyethylene | Sodium 5-sulfoisophthalate | Esterification or ester interchange catalyst | |
| | Biomass-derived Type | Fossil resource-based Type | Dicarboxylic acid component Type | glycol wt % (vs. PET) | mol % (vs. total dicarboxylic acid component) | Type | Blending amount (ppm) (equivalent, atom basis) |
| Comparative Example 26 | — | Reference Example 6 | TPA | 1 | 2 | — | — |
| Comparative Example 27 | — | Reference Example 6 | TPA | 1 | 2 | — | — |
| Comparative Example 28 | — | Reference Example 6 | TPA | 1 | 2 | — | — |
| Comparative Example 29 | — | Reference Example 6 | TPA | 1 | 2 | — | — |
| Comparative Example 30 | — | Reference Example 6 | TPA | 1 | 2 | — | — |

EG: Ethylene glycol
TPA: Terephthalic acid
DMT: Dimethyl terephthalate
MGA: Magnesium acetate

TABLE 6

| | Catalyst 2 | | Additives | | | | |
|---|---|---|---|---|---|---|---|
| | Polymerization catalyst | | Phosphorus compound | | Other additive | | |
| | Type | Blending amount (ppm) (equivalent, atom basis) | Type | Blending amount (ppm) (equivalent, atom basis) | Type | Blending amount (ppm) (equivalent, atom basis) | $TiO_2$ Blending amount (wt %) |
| Comparative Example 1 | $Sb_2O_3$ | 250 | TMPA | 50 | — | — | 0.1 |
| Comparative Example 2 | $Sb_2O_3$ | 250 | TMPA | 50 | — | — | 0.1 |
| Comparative Example 3 | $Sb_2O_3$ | 250 | TMPA | 20 | — | — | 0.1 |
| Comparative Example 4 | $Sb_2O_3$ | 250 | TMPA | 20 | — | — | 0.1 |
| Comparative Example 5 | $Sb_2O_3$ | 250 | TMPA | 20 | — | — | 0.1 |
| Comparative Example 6 | $Sb_2O_3$ | 250 | TMPA | 50 | — | — | 0.1 |
| Comparative Example 7 | $Sb_2O_3$ | 250 | TMPA | 50 | — | — | 0.1 |
| Comparative Example 8 | $Sb_2O_3$ | 250 | TMPA | 20 | — | — | 0.1 |
| Comparative Example 9 | $Sb_2O_3$ | 250 | TMPA | 20 | — | — | 0.1 |
| Comparative Example 10 | $Sb_2O_3$ | 250 | TMPA | 20 | — | — | 0.1 |
| Comparative Example 11 | $Sb_2O_3$ | 250 | TMPA | 20 | — | — | 0.1 |
| Comparative Example 12 | $Sb_2O_3$ | 250 | TMPA | 50 | — | — | 0.1 |
| Comparative Example 13 | $Sb_2O_3$ | 250 | TMPA | 50 | — | — | 0.1 |
| Comparative Example 14 | $Sb_2O_3$ | 250 | TMPA | 20 | — | — | 0.1 |
| Comparative Example 15 | $Sb_2O_3$ | 250 | TMPA | 20 | — | — | 0.1 |
| Comparative Example 16 | $Sb_2O_3$ | 250 | TMPA | 20 | — | — | 0.1 |
| Comparative Example 17 | $Sb_2O_3$ | 250 | TMPA | 20 | — | — | 0.1 |
| Comparative Example 18 | $Sb_2O_3$ | 250 | TMPA | 50 | — | — | 0.1 |
| Comparative Example 19 | $Sb_2O_3$ | 250 | TMPA | 50 | — | — | 0.1 |
| Comparative Example 20 | $Sb_2O_3$ | 250 | TMPA | 20 | — | — | 0.1 |

TABLE 6-continued

|  | Catalyst 2 | | Additives | | | | |
|---|---|---|---|---|---|---|---|
|  | Polymerization catalyst | | Phosphorus compound | | Other additive | | |
|  | Type | Blending amount (ppm) (equivalent, atom basis) | Type | Blending amount (ppm) (equivalent, atom basis) | Type | Blending amount (ppm) (equivalent, atom basis) | TiO$_2$ Blending amount (wt %) |
| Comparative Example 21 | Sb$_2$O$_3$ | 250 | TMPA | 20 | — | — | 0.1 |
| Comparative Example 22 | Sb$_2$O$_3$ | 250 | TMPA | 20 | — | — | 0.1 |
| Comparative Example 23 | Sb$_2$O$_3$ | 250 | PA | 20 | — | — | 0.1 |
| Comparative Example 24 | Citric acid Ti | 5 | TMPA | 25 | MGA | 30 | 0.1 |
| Comparative Example 25 | Mannitol Ti | 5 | TMPA | 25 | MGA | 30 | 0.1 |
| Comparative Example 26 | Basic Aluminium Acetate | 20 | TMPA | 25 | MGA | 30 | 0.1 |
| Comparative Example 27 | Mannitol Ti | 5 | PA | 25 | MGA | 30 | 0.1 |
| Comparative Example 28 | Mannitol Ti | 5 | PEP36 | 25 | MGA | 30 | 0.1 |
| Comparative Example 29 | Mannitol Ti | 5 | GSY | 25 | MGA | 30 | 0.1 |
| Comparative Example 30 | Sb$_2$O$_3$ | 250 | TMPA | 20 | — | — | 0 |

Sb$_2$O$_3$: Antimony trioxide
TMPA: Trimethyl phosphate
Citric acid Ti: Citric acid chelate titanium complex
PA: Phosphoric acid
Mannitol Ti: Mannitol chelate titanium complex
TiO$_2$: Titanium oxide
PEP36: 3,9-Bis(2,6-di-t-butyl-4-methylphenoxy)-2,4,8,10-tetraoxa-3,9-diphosphaspiro[5,5]undecane (manufactured by ADEKA CORPORATION)
GSY: Tetrakis(2,4-di-t-butyl-5-methylphenyl)[1,1-biphenyl]-4,4'-diylbisphosphonite (manufactured by Osaki Industry Co., Ltd.)

TABLE 7

|  | Polymer characteristics | | | | | | | |
|---|---|---|---|---|---|---|---|---|
|  | Polymerization time | Intrinsic viscosity | | Color tone | | | DEG content | Content of 1,2-PD-derived components | Biobased content |
|  | (hr:min) | IV [dl/g] | ΔIV [dl/g] | L value | a value | b value | [wt %] | [ppm] | [%] |
| Comparative Example 1 | 3:03 | 0.666 | 0.125 | 64 | −4.1 | 14 | 1.5 | 633 | 20 |
| Comparative Example 2 | 3:08 | 0.663 | 0.121 | 64 | −4.4 | 2 | 1.8 | lower than minimum detection limit | 0 |
| Comparative Example 3 | 3:05 | 0.667 | 0.129 | 66 | −2.4 | 12 | 1.6 | 627 | 20 |
| Comparative Example 4 | 3:01 | 0.664 | 0.127 | 66 | −2.3 | 13 | 1.5 | 681 | 20 |
| Comparative Example 5 | 3:07 | 0.665 | 0.125 | 66 | −2.5 | 2 | 1.4 | lower than minimum detection limit | 0 |
| Comparative Example 6 | 3:12 | 0.703 | 0.135 | 64 | −4.3 | 14 | 1.8 | 621 | 20 |
| Comparative Example 7 | 3.16 | 0.701 | 0.138 | 63 | −4.6 | 10 | 1.5 | lower than minimum detection limit | 0 |
| Comparative Example 8 | 3:13 | 0.701 | 0.135 | 64 | −2.6 | 13 | 1.7 | 618 | 20 |
| Comparative Example 9 | 2.55 | 0.754 | 0.161 | 66 | −3.3 | 16 | 1.9 | 581 | 18 |
| Comparative Example 10 | 3:13 | 0.704 | 0.139 | 62 | −2.5 | 14 | 1.6 | 682 | 20 |

TABLE 7-continued

| | | Polymer characteristics | | | | | | | |
|---|---|---|---|---|---|---|---|---|---|
| | Polymerization time | Intrinsic viscosity | | Color tone | | | DEG content | Content of 1,2-PD-derived components | Biobased content |
| | (hr:min) | IV [dl/g] | ΔIV [dl/g] | L value | a value | b value | [wt %] | [ppm] | [%] |
| Comparative Example 11 | 3:14 | 0.705 | 0.141 | 63 | −2.7 | 10 | 1.7 | lower than minimum detection limit | 0 |
| Comparative Example 12 | 3:03 | 0.625 | 0.147 | 66 | −4.3 | 14 | 2.1 | 628 | 20 |
| Comparative Example 13 | 3:07 | 0.627 | 0.132 | 65 | −4.1 | 11 | 2.2 | lower than minimum detection limit | 0 |
| Comparative Example 14 | 3:03 | 0.625 | 0.137 | 66 | −2.6 | 15 | 2.4 | 631 | 20 |
| Comparative Example 15 | 2:50 | 0.503 | 0.185 | 69 | −3.4 | 17 | 2.1 | 602 | 20 |
| Comparative Example 16 | 3:04 | 0.627 | 0.145 | 66 | −2.6 | 15 | 2.3 | 683 | 20 |
| Comparative Example 17 | 3:01 | 0.621 | 0.148 | 66 | −2.3 | 10 | 2.1 | lower than minimum detection limit | 0 |
| Comparative Example 18 | 3:06 | 0.691 | 0.188 | 66 | −4.5 | 14 | 2.3 | 619 | 20 |
| Comparative Example 19 | 3:02 | 0.696 | 0.181 | 66 | −4.2 | 12 | 2.2 | lower than minimum detection limit | 0 |
| Comparative Example 20 | 3:06 | 0.698 | 0.188 | 66 | −2.5 | 15 | 2.4 | 622 | 20 |
| Comparative Example 21 | 3:05 | 0.695 | 0.182 | 66 | −2.4 | 14 | 2.3 | 677 | 20 |
| Comparative Example 22 | 3:02 | 0.692 | 0.189 | 66 | −2.7 | 10 | 2.3 | lower than minimum detection limit | 0 |
| Comparative Example 23 | 3:04 | 0.698 | 0.189 | 66 | −2.3 | 10 | 2.3 | lower than minimum detection limit | 0 |
| Comparative Example 24 | 3:05 | 0.691 | 0.198 | 69 | −5.4 | 15 | 2.3 | lower than minimum detection limit | 0 |
| Comparative Example 25 | 3:01 | 0.696 | 0.185 | 69 | −5.3 | 12 | 2.1 | lower than minimum detection limit | 0 |
| Comparative Example 26 | 3:09 | 0.693 | 0.192 | 64 | −3.6 | 10 | 2.1 | lower than minimum detection limit | 0 |
| Comparative Example 27 | 3:10 | 0.695 | 0.191 | 69 | −4.7 | 12 | 2.2 | lower than minimum detection limit | 0 |
| Comparative Example 28 | 3:05 | 0.694 | 0.185 | 69 | −3.5 | 12 | 2.3 | lower than minimum detection limit | 0 |
| Comparative Example 29 | 3:07 | 0.697 | 0.184 | 69 | −3.8 | 12 | 2.1 | lower than minimum detection limit | 0 |
| Comparative Example 30 | 3:06 | 0.692 | 0.198 | 56 | −1.7 | 9 | 2.2 | lower than minimum detection limit | 0 |

DEG: Diethylene glycol
1,2-PD: 1,2-Propanediol
1,2-PD detection limit: 15 ppm

Comparative Examples 31 to 60

The polyethylene terephthalate pellets obtained in Comparative Example 1 to 30 were subjected to spinning and drawing in the same manner as Working Example 27. During this process, an accumulation of deposits was observed on the spinneret area, and broken thread incidents occurred. Measurement results for the accumulation of deposits on the spinneret area, frequency of broken thread, and strength and elongation of the drawn thread are summarized in Table 8.

TABLE 8

| | Input polymer No. of corresponding comparative example | Accumulation of deposits on spinneret area and frequency of broken thread | Strength (cN/dtex) | Elongation (%) |
|---|---|---|---|---|
| Comparative Example 31 | 1 | X | 4.1 | 38 |
| Comparative Example 32 | 2 | X | 4.1 | 38 |
| Comparative Example 33 | 3 | X | 4.1 | 38 |
| Comparative Example 34 | 4 | X | 4.1 | 38 |
| Comparative Example 35 | 5 | X | 4.1 | 38 |
| Comparative Example 36 | 6 | X | 3.8 | 40 |
| Comparative Example 37 | 7 | X | 3.8 | 40 |
| Comparative Example 38 | 8 | X | 3.7 | 40 |
| Comparative Example 39 | 9 | X | 2.8 | 25 |
| Comparative Example 40 | 10 | X | 3.7 | 40 |
| Comparative Example 41 | 11 | X | 3.7 | 40 |
| Comparative Example 42 | 12 | X | 3.7 | 40 |
| Comparative Example 43 | 13 | X | 3.7 | 40 |
| Comparative Example 44 | 14 | X | 3.7 | 40 |
| Comparative Example 45 | 15 | X | 2.1 | 25 |
| Comparative Example 46 | 16 | X | 3.7 | 40 |
| Comparative Example 47 | 17 | X | 3.7 | 40 |
| Comparative Example 48 | 18 | X | 3.6 | 40 |
| Comparative Example 49 | 19 | X | 3.6 | 40 |
| Comparative Example 50 | 20 | X | 3.6 | 40 |
| Comparative Example 51 | 21 | X | 3.6 | 40 |
| Comparative Example 52 | 22 | X | 3.6 | 40 |
| Comparative Example 53 | 23 | X | 3.6 | 40 |
| Comparative Example 54 | 24 | X | 3.6 | 40 |
| Comparative Example 55 | 25 | X | 3.6 | 40 |
| Comparative Example 56 | 26 | X | 3.6 | 40 |
| Comparative Example 57 | 27 | X | 3.6 | 40 |
| Comparative Example 58 | 28 | X | 3.6 | 40 |
| Comparative Example 59 | 29 | X | 3.6 | 40 |
| Comparative Example 60 | 30 | X | 3.6 | 40 |

The invention claimed is:

1. A polyester obtained from a dicarboxylic acid and/or an ester-forming derivative thereof, and an ethylene glycol, a catalyst selected from the group consisting of a titanium compound, aluminum compound and antimony compound, a phosphorous compound selected from the group consisting of phosphoric acid, trimethyl phosphate, ethyl diethylphosphonoacetate, 3,9-bis(2,6-di-t-butyl-4-methylphenoxy)-2,4,8,10-tetraoxa-3,9-diphosphaspiro[5,5]undecane and tetrakis(2,4-di-t-butyl-5-methylphenyl) [1,1-biphenyl]-4,4'-diylbisphosphonite, wherein the polyester contains 15 to 203 ppm of a sum of copolymerized 1,2-propanediol and/or uncopolymerized 1,2-propanediol, and wherein a thermostability index ($\Delta IV$) of the polyester is 0.051 to 0.069 dl/g.

2. The polyester described in claim 1, containing a 5-sulfoisophthalic acid salt and/or an ester-forming derivative thereof as copolymerization components.

3. The polyester as described in claim 1, containing a polyoxyalkylene glycol with a molecular weight of 500 to 20,000 as a copolymerization component.

4. Moldings produced from a polyester as described in claim 1.

5. A method of manufacturing the polyester described in claim 1, comprising subjecting a dicarboxylic acid and/or an ester-forming derivative thereof, and an ethylene glycol to an esterification or ester interchange reaction and performing a condensation polymerization reaction under reduced pressure, wherein the ethylene glycol has a 1,2-propanediol content of 45 to 1,000 ppm.

6. The polyester described in claim 1, wherein ethylene glycol is biomass-derived ethylene glycol.

* * * * *